United States Patent [19]

Sale

[11] Patent Number: 4,804,936
[45] Date of Patent: Feb. 14, 1989

[54] LIQUID SELECTIVE AUTOMATIC BILGE PUMP CONTROL

[75] Inventor: Ronald G. S. Sale, Saanichton, Canada

[73] Assignee: Saler Electronic Systems, Inc., Canada

[21] Appl. No.: 29,785

[22] Filed: Mar. 25, 1987

Related U.S. Application Data

[62] Division of Ser. No. 817,983, Jan. 13, 1986, abandoned.

[51] Int. Cl.⁴ .......................................... H01C 10/02
[52] U.S. Cl. ...................................... 338/80; 338/28; 324/446
[58] Field of Search ................ 338/28, 34, 80, 81, 338/82, 83, 84, 85, 86; 324/446, 447, 448, 449; 219/273

[56] References Cited

U.S. PATENT DOCUMENTS

| | | | |
|---|---|---|---|
| 4,125,822 | 11/1978 | Perren et al. | 338/34 |
| 4,382,173 | 5/1983 | Howard-Leicester | 219/273 |
| 4,507,521 | 3/1985 | Goellner | 324/448 X |
| 4,626,786 | 12/1986 | Bödecker et al. | 324/449 |
| 4,638,291 | 1/1987 | Puscasu | 338/28 X |

Primary Examiner—E. A. Goldberg
Assistant Examiner—M. M. Lateef
Attorney, Agent, or Firm—Martin Fruitman

[57] ABSTRACT

A highly reliable bilge pump control system which distinguishes between oil and water and operates without a mechanical float switch. It uses a conductivity type probe of special construction which is unaffected by sludge and contamination at the oil-water interface. Multiple probes at varying depths feed high impedance operational amplifiers which operate a conventional pump through digital circuitry which assures that no oil is pumped from the bilge.

8 Claims, 3 Drawing Sheets

LIQUID SELECTIVE AUTOMATIC BILGE PUMP CONTROL

This is a division of application Ser. No. 06/817,983 filed 1/13/86 now abandoned.

SUMMARY OF THE INVENTION

This invention deals generally with measuring and more specifically with a liquid level detection and control system which uses an immersible electrode type sensor.

Bilge pumps must be as old as ships themselves, and automatic bilge pumps, operating only when the bilge accumulates a certain amount of liquid, are also not new. However, what is relatively recent are stringent environmental regulations which forbid the discharge of hydrocarbons or other environment contaminating liquids from water crafts. Where such regulations are in effect it is impossible to legally use the typical automatic bilge pump. Such systems are usually controlled by a float switch, and such switches cannot distinguish between water and hydrocarbons. Use of the automatic feature of the bilge pump therefore involves the risk of illegally discharging oil or other contaminates from the vessel.

Conductance probes can also be used to activate bilge pump systems, but the problem with those probes which are generally available is that in the presence of an oil-water interface they tend to trap or be coated by oil and therefore become unable to function reliably.

The present invention solves these problems, first, by the use of specially constructed conductance probes which avoid contamination by oil, and also by the use of an electronic control circuit which uses digital signals to achieve reliable operation by distinguishing valid signals from error producing conditions.

The probe of the present invention is essentially constructed as an inverted cup. Its general configuration is of a fingerlike hollow cylinder, or shroud, with one end, its upper end, sealed off with an insulator, through which a conductive rod electrode passes. The electrode extends beyond the open end of the hollow cylinder and then bends in an acute angle. The electrode extends beyond the projection of the hollow cylinder before it terminates, so that the radial distance from the major length of the electrode to its tip is greater than the radius of the cylinder.

This particular construction yields specific advantages for the probe while it is in use. Because of it, the shroud structure traps air within it as a liquid rises and covers the probe's open end. The air compressed within the shroud protects the internal insulators from being wetted and assures that the moisture will not provide a leakage path to ground through the probe mounting hardware. The length of the shroud is selected so that it will be long enough to assure that, for the depth of immersion at which it will be used, the volume of air within it will be sufficient to maintain its internal insulators dry.

In the preferred embodiment of the pumping system, the control system for the bilge pump uses as many as four of the probes, one each for a circuit return, a pump "on" level, a pump "off" level, and an "alarm" level. These probes are interconnected to a logic circuit which controls a conventional bilge pump so that it is turned on at one level of water in the bilge and is shut off only when the water level has decreased below another prescribed level. These levels are determined for the individual application by location of the probes within the vessel.

In order to facilitate mounting the probes in the vessel, the probes are constructed to fit into a separately mounted clip.

The mounting or relocation of probes thus becomes a simple matter of removing the probe from its holder, locating the holder, and reinserting the probe. This permits physically relocating a probe without any concern for affecting the electrical circuitry.

The logic circuit which controls the pump also provides unique data on the status of the system. It will, for instance, indicate how often the pump operated. This tells the operator the speed at which the bilge is taking on water. Moreover, the logic circuit includes provisions for both remote and local testing of the sensing and pumping system and back-up circuitry is also included to provide audible and visual alarms if there should be a malfunction.

In total, the present invention provides an automatic liquid pumping system which distinguishes between water and hydrocarbons, which pumps only the water and which records its operation for analysis. Moreover, it does all this with no mechanical parts, except for the pump, and therefore has superior reliability and little susceptibility to damage by floating debris.

DETAILED DESCRIPTION OF THE INVENTION

Figure 1:
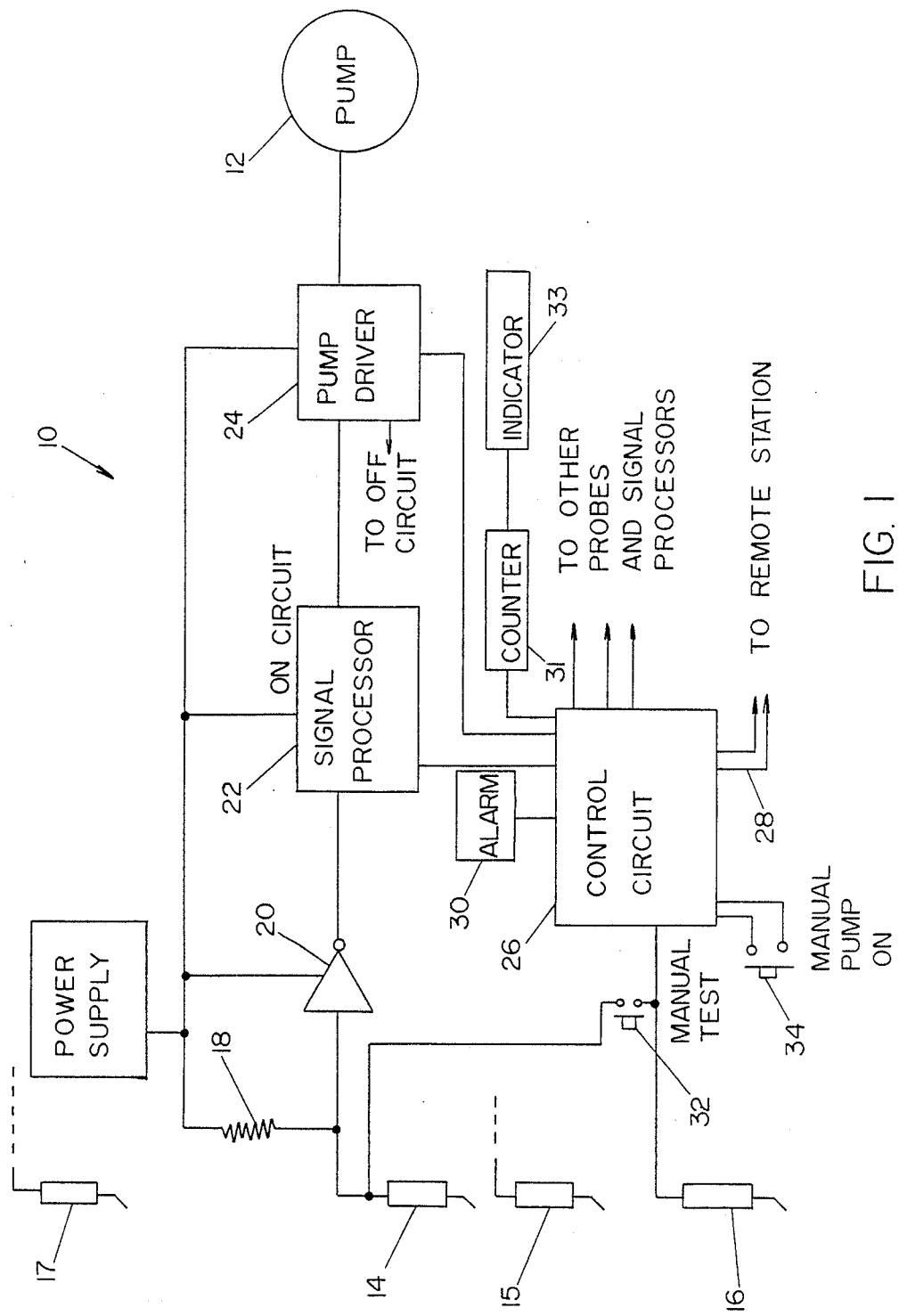
FIG. 1 is a schematic block diagram of the electronic circuit of the preferred embodiment.

The electronic circuit of the preferred embodiment of the invention is shown in FIG. 1 in the schematic block diagram form in which automatic bilge pump control 10 operates pump 12 based on the liquid level sensed by "On Level" probe 14 and "Off Level" probe 15.

Circuit return probe 16 is used to furnish an independent electronic circuit return, and "Alarm Level" probe 17 is located at a point in the bilge higher than "On" probe 14. This location permits it to act as a back-up, to operate pump 12 if the normal turn-on circuit 10 malfunctions. The four probes are schematically represented in FIG. 1 with their appropriate vertical orientation relative to each other, that is, in actual use "Alarm" probe 17 is the uppermost, "On" probe 14 is the next highest, "Off" probe 15 is the next highest, and circuit return probe 16 is the lowest.

The electronic circuits used with probes 14, 15 and 17 are all essentially similar, so for clarity and ease of description the circuit is depicted only once in FIG. 1 in relation to probe 14. Automatic bilge pump control 10 is essentially a very high input impedance circuit using very low sensing currents at probe 14. This feature is vitally important in the operation of the system because, although water and the typical oil floating atop it vary significantly in their conductivity, in actual practice an intermediate zone of oil-water emulsion tends to exist in the area where the two fluids meet. This emulsion, which is formed because of the effects of the detergents which are present in the typical available oils, causes the interface between the water and oil in ship bilges to be much less distinct that might be supposed. The conductivity at the oil-water interface therefore does not change in a step function but rather somewhat gradually. The electrical signal resulting from such a situation is a ramp, and a high input impedance circuit is required to maintain this signal at levels which permit detection of the lowest edge of the emulsion, in order to stop the pump before that contaminate is pumped out into the environment. The typical input impedance used in the preferred embodiment is 10 megohm, which is the value of resistor 18.

In the preferred embodiment the signal developed at the junction of resistor 18 and probe 14 is fed to the input of operational amplifier 20 from which it is fed to signal processor 22. Signal processor 22, uses conventional amplification and analog-to-digital conversion circuits. Signal processor 22 then feeds signals to control circuit 26 and also to pump driver 24, which, in turn operates pump 12.

"Off" probe 15 is connected to similar circuit elements (not shown) and its signal path also feeds into the pump driver, with the exception that it operates in a reverse mode. "On" probe 14 and its circuit, of course, act to turn pump 12 on when probe 14 begins to conduct a certain quantity of current as the rising liquid level raises the less conductive oil and emulsion past the probe and the water below the oil contacts probe 14. Once the pump begins to operate, control circuit 26 and pump driver 24 disregard any change in the status of "On" probe 14 and instead monitor "Off" probe 15.

At probe 15, the falling level of liquid caused by the action of pump 12 causes the current which was greater because of the immersion in more highly conductive water to be reduced as the oil-water emulsion first contacts probe 15. It is this change which initiates the signal used to turn off pump 12, and to switch the system to monitoring "On" probe 14 again. The input of pump 12 is, of course, located at a liquid level which is below "Off" probe 15.

Circuit return probe 16 also has a particularly beneficial action, because of the high impedance signals of the other probes. It permits the use of an ungrounded circuit which, in turn, reduces the likelihood of the occurence of stray ground current which would give false indications of liquid levels. Such stray ground currents are more likely when the ship hull or ship electrical system is itself the circuit return.

"Alarm" probe 17 operates through an independent circuit similar to that of probe 14 and including an independent pump driver circuit. Regardless of the status of any other probes or circuits, if "Alarm" probe 17 conducts current, its circuit acts independently to start pump 12 and to initiate alarm circuit 30 within control circuit 26. Alarm circuit 30 not only operates an audible alarm, but also records and counts the alarm action for future analysis of the system. It can also be used to activate remote indicators of other alarm systems. By its use, for instance, wires 28 are activated to activate remote indicators to inform security personnel that there has been a bilge pump system malfunction.

Control circuit 26 also uses the digital signals produced by signal processor 22 and its counterparts associated with the other probes to record the actions of the system, to analyse its actions, and even to judge the amount of water leaking into the ship's bilge. The basis of all these actions are the digital signals fed from the signal processors.

For example counter 31 maintains a record of, and indicator 33 displays, the number of times the pump operates in a specific period of time, for instance eight hours, thereby indicating the amount of water pumped from the bilge, and therefore determines the amount of water leaking into the bilge in that period.

Another feature of control circuit 26 is remote testing of each liquid level probe circuit. By activating manual test switch 32 the bilge pump start circuit can be tested even though no water is actually present. Similar manual test switches for the pump off circuit and the alarm circuit are also included in control circuit 26. Manual "pump on" switch 34 permits testing of pump 12 itself for aid in servicing the system or for lowering the liquid level to a point below "Off" probe 15.

The present invention furnishes a completely automatic bilge pump system which is highly reliable because it has no moving parts other than the pump, but also has the ability to distinguish between water, which should be pumped, and oil or other contaminates which must not be pumped.

This selectivity is available not only because of the circuit configuration but also because of the unique construction of the conductivity probes, such as probe 14, which are used in the system. The construction of probe 14 is shown in FIG. 2 which is a side cross-section view.

Figure 2:
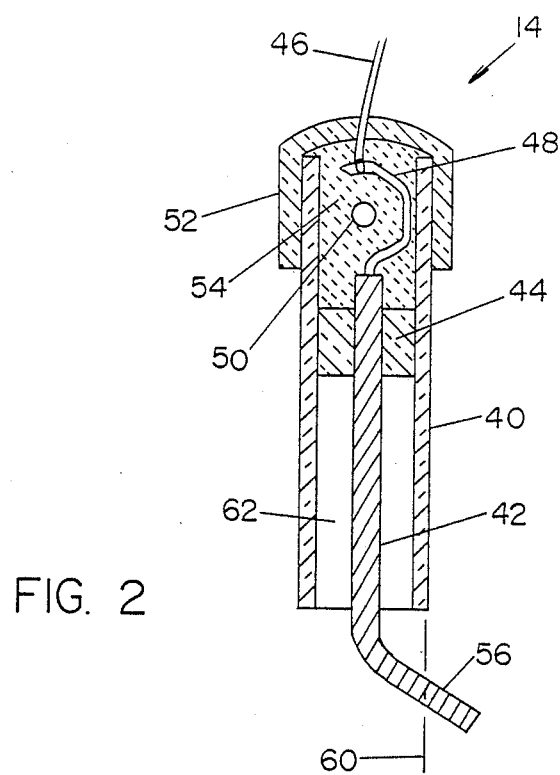
FIG. 2 is a cross-section view of the liquid level probe of the preferred embodiment.

As shown in FIG. 2, probe 14 is essentially a hollow body 40 of electrically insulating material with a central conductive rod 42 extending out its lower end. In the preferred embodiment body 40 is a cylinder. Rod 42 is held in place by insulator 44 and connected to wire 46 by wire loop 48 which is bent to avoid mounting hole 50. Cap 52 is bonded to the top of body 40 and the volume above insulator 44 (except for mounting hole 50) is encapsulated with filler 54 to assure that no air leakage can occur through the upper end of cylinder 40.

Angular section 56 of rod 42 is, perhaps, the most important feature of probe 14. It is bent at an acute angle to the axis of body cylinder 40 and the length of angular section 56 is such that it extends beyond projection line 60 of the outside surface of body 40. It is this configuration which aids probe 14 in resisting electrical problems from oils, emulsions and other contaminates.

One such problem is the possibility that a conductive film will form across insulator 44 and the surfaces of body 40 to short the probe to ground. It is the hollow cylinder construction with air space 62 inside, which prevents such problems. As liquid rises to the open end of hollow body cylinder 40, the liquid traps air within air space 62. Although this trapped air compresses somewhat as the liquid rises further, the air pocket prevents liquid from contacting insulator 44 and large portions of the interior of hollow body 40. The air pocket therefore prevents these surfaces from being contaminated and from causing electrical leakaage to ground or the circuit return.

Bent section 56 of conductive rod 42 has somewhat the opposite action. With a more typical electrode system which would be completely within the downward projection of hollow body 40, there is the possibility of an insulating bubble of oil forming. For instance, as the oil layer on top of the bilge water rises, hollow body cylinder 40 may trap a section of oil beneath it, when it acts like a cookie cutter to sever a circular "slice" of the oil layer from the rest of the layer. If this "slice" is thick enough it can extend below the end of conductive rod 42, and make it appear electrically as if the water level never reached conductive rod 42.

This very real problem is avoided by the extension of conductive rod 42 beyond the downward projection of body 40. By bending section 56 at an acute angle the first contact with a liquid is still defined by the end of rod 42, but the end can not be covered by a trapped oil bubble since there is no trapping structure above it. The problem of inadvertant insulation by trapped oil is thereby avoided.

Figure 3:
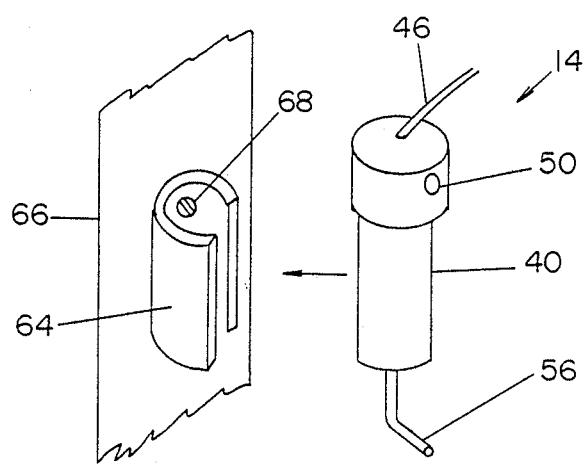
FIG. 3 is a pictorial view of the mounting system of the liquid level probe.

FIG. 3 pictorially depicts the two mounting systems available for probe 14. The first is simply mounting hole 50 which is drilled or cast through the top of probe 14. By this means, probe 14 can easily be mounted to any surface with a through bolt or screw (not shown).

A somewhat more versatile mounting system is also shown in FIG. 3. It is spring mounting clip 64. Clip 64 is simply attached to a typical surface 66 by screw 68, and probe 14 is snapped into it with rod end 56 aimed away from surface 64. The particular benefit of the use of spring clips such as clip 64 is that several clips can be located at various levels within the ship's bilge, and as long as connecting wire 46 is of the correct length, probe 14 can be moved among several clips to place it at the most advantageous location in actual service.

Figure 4:
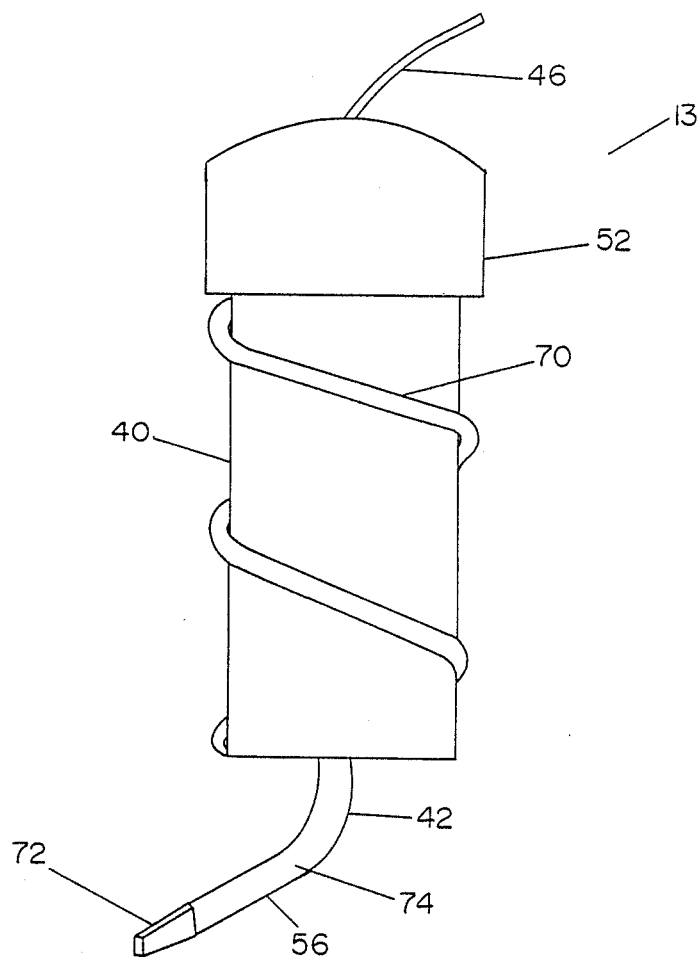
FIG. 4 is a pictorial representation of an alternate embodiment of the liquid level probe of the invention.

FIG. 4 shows an alternate embodiment of the probe of the present invention which includes features to aid in releasing oil which has once contacted the probe. Although probe 13 of FIG. 4 is otherwise constructed similar to probe 14 of FIG. 2, it also has helical agitator 70 on the outside of cylinder 40 and angular section 56 of rod 42 terminates with tip structure 72. Also bent section 56 and rod 42 are coated with low friction material 74 such as polyethylene or other plastic.

Agitator 70 acts to disturb and break up the movement of the bilge oil layer as it rises or falls past cylinder 40 so that the oil layer will not, in effect, merely deflect or distort causing an error in the sensing procedure. With the installation of agitator 70 on the outside of cylinder 40, the oil level is severed to the extent necessary to have it move smoothly past the probe.

Tip structure 72 on angular section 56 of rod 42 serves a similar purpose. Particularly for very viscous oil, as the oil layer falls down past the rod tip, there is sometimes a tendency for the oil to cling to the tip and to form a tendril of oil hanging from the tip to the lower layer of oil. The thin, flat-sided, knife-like tip configuration of tip 72, with the large sides oriented generally vertical avoids the formation of this tendril by essentially cutting the clinging oil so it falls off the tip.

To further resist the tendency of oil to be retained on rod 42 and angular section 56, a low friction material such as polyethylene or some other plastic is coated around all portions of rod 42 except for the conductive tip. With the coating on rod 42, there is much less tendency of oil to be retained on rod 42 and it does not gravitate to the tip where it may affect the conductivity.

With or without the special features shown in FIG. 4, the probe of the present invention serves the special purpose of sensing the presence of the top surface of the bilge water, and in combination with the circuit of the invention it reliably distinguishes that water surface from oil atop it. It, therefore, permits the operation of an automatic bilge pump system which, without an observing operator, will pump only water out into the environment and will stop the pumping action before any contamination is discharged.

It is to be understood that the form of this invention as shown is merely a preferred embodiment. Various changes may be made in the function and arrangement of parts; equivalent means may be substituted for those illustrated and described; and certain features may be used independently from others without departing from the spirit and scope of the invention as defined in the following claims.

For example, agitator 70 of FIG. 4 could be constructed in a configuration other than a helix, or cap 52 of probe 14 could be integral with cylinder 40.

What is claimed as new and for which Letters Patent of the United States are desired to be secured is:

1. A conductivity probe which can distinguish between a first conductive liquid and another liquid of different conductivity within a layer adjacent to the first conductive liquid, comprising:
   a hollow body sealed at one end to prevent air from escaping through that end;
   an electrode structure suspended within the hollow body, so that it is electrically insulated from the body, and extends out the unsealed end of the body, with a section of the electrode structure which extends outside the body being oriented so that it also extends sideward beyond the projection line of the body;
   an electrical conductor attached to the electrode structure and permiting an electrical connection to the electrode structure from outside the body; and
   mounting means which permits the conductivity probe to be attached to an external surface so that the unsealed end of the body is oriented below the sealed end.

2. The conductivity probe of claim 1 wherein the hollow body is a cylinder.

3. The conductivity probe of claim 1 wherein the electrode structure is a centrally located rod and the section which extends outside the body is ent at an acute angle to the centrally located portion of rod.

4. The conductivity probe of claim 1 wherein the mounting means is a spring clip into which the hollow body inserts.

5. The conductivity probe of claim 1 further including a shaped tip upon the electrode structure with a knife-like structure comprising two flat sides located parallel to each other with a small separation between them and with the flat sides oriented generally in the vertical plane when the probe is in use.

6. The conductivity probe of claim 1 further including an agitator structure attached to the outside of the hollow body to disturb the vertical movement of liquid along the outside of the hollow body.

7. The conductivity probe of claim 1 further including a helical agitator structure attached to the outside of the hollow body to disturb the vertical movement of liquid along the outside of the hollow body.

8. The conductivity probe of claim 1 further including a low friction coating on all but the tip of the electrode structure.

* * * * *